US00PP26846P3

(12) United States Plant Patent
Klemm et al.

(10) Patent No.: US PP26,846 P3
(45) Date of Patent: Jun. 21, 2016

(54) ***DIANTHUS* PLANT NAMED 'KLEDP14206'**

(50) Latin Name: *Dianthus caryophyllus*
Varietal Denomination: KLEDP14206

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 87 days.

(21) Appl. No.: 14/120,456

(22) Filed: May 20, 2014

(65) Prior Publication Data

US 2015/0342106 P1 Nov. 26, 2015

(51) Int. Cl.
*A01H 5/02* (2006.01)

(52) U.S. Cl.
USPC ..... Plt./273

(58) Field of Classification Search
USPC ..... Plt./273, 272, 277, 278
See application file for complete search history.

*Primary Examiner* — June Hwu
(74) *Attorney, Agent, or Firm* — James M. Weatherly; Bethany R. Roahrig; Cochran Freund & Young, LLC

(57) ABSTRACT

A new *Dianthus* plant particularly distinguished by having double flowers with a dark pink, purple bicolor, and an upright plant habit, is disclosed.

1 Drawing Sheet

Genus and species: *Dianthus caryophyllus*.
Variety denomination: 'KLEDP14206'.

BACKGROUND OF THE NEW PLANT

The present invention comprises a new and distinct variety of *Dianthus*, botanically known as *Dianthus caryophyllus* and hereinafter referred to by the variety name 'KLEDP14206'. 'KLEDP14206' originated from a branch mutation of the proprietary female parent 'DCP 2009-1003' (unpatented) in May 2010 in a greenhouse in Latina, Italy.

In 2010 'KLEDP14206' was first vegetatively propagated by vegetative cuttings. 'KLEDP14206' was found to reproduce true to type in successive generations of asexual propagation in Stuttgart, Germany via stem cuttings.

SUMMARY

The following are the most outstanding and distinguishing characteristics of this new variety when grown under normal horticultural practices in Stuttgart, Germany.

1. Double flowers with a dark pink, purple bicolor; and
2. An upright plant habit.

DESCRIPTION OF THE PHOTOGRAPH

This new *Dianthus* plant is illustrated by the accompanying photograph which shows an overall view of the plant. The colors shown are as true as can be reasonably obtained by conventional photographic procedures.

The photograph shows the overall plant habit of the plant. The plant is about 5 months-old grown in Stuttgart, Germany in May 2012.

DESCRIPTION OF THE NEW VARIETY

The following detailed descriptions set forth the distinctive characteristics of 'KLEDP14206'. The data which define these characteristics were collected from asexual reproductions carried out in Stuttgart, Germany. Data was collected on five month-old plants grown in a greenhouse in Stuttgart, Germany in February 2014. Color references are to The R.H.S. Colour Chart of The Royal Horticultural Society of London (R.H.S.), 5$^{th}$ edition (2007).

Classification:
- *Family*.—Caryophyllaceae.
- *Species*.—*Dianthus caryophyllus*.
- *Common name*.—Pot carnation.
- *Variety*.—'KLEDP14206'.

Parentage: Result of a mutation of the proprietary *Dianthus* plant 'DCP 2009 1003'.

Propagation:
- *Type*.—Vegetative cuttings.
- *Time to produce a rooted young plant*.—14 to 16 days.
- *Root description*.—White, fine.
- *Rooting habit*.—Lanceolate.

Plant description:
- *Plant form*.—Potted plant, upright.
- *Plant height*.—13.0 cm to 15.0 cm.
- *Plant diameter or spread*.—20.0 cm to 22.0 cm.

Lateral branches:
- *General description*.—Stem is solid.
- *Length*.—8.0 to 10.0 cm.
- *Diameter*.—3.0 to 5.0 cm.
- *Internode length*.—0.6 cm to 0.8 cm.
- *Number of internodes per stem*.—Four.
- *Node length*.—0.3 cm.
- *Node diameter*.—0.3 cm.
- *Texture*.—Smooth.
- *Color*.—RHS N137B.

Foliage description:
- *Arrangement*.—Opposite.
- *Length*.—4.0 to 6.0 cm.
- *Width*.—0.6 cm to 0.8 cm.
- *Shape*.—Lanceolate.
- *Apex*.—Acute.

*Base*.—Obtuse.
*Margin*.—Entire.
*Texture*.—Upper and lower surfaces: Smooth.
*Venation pattern*.—Parallel.
*Color*.—Immature leaves: Upper surface: RHS 138A. Lower surface: RHS 147B. Mature leaves: Upper surfaces: RHS N139A. Lower surface: RHS N137A. Venation: RHS N139A.

Flower description:
*Flower type and habit*.—Double, round, small sprays.
*Fragrance*.—Present.
*Natural flowering season*.—Spring to Fall.
*Flower longevity*.—10 to 12 days.
*Number of flowers per spray*.—3-5.
*Flowers in relation with the foliage*.—Slightly above.
*Flower buds*.—Length: 1.8 cm to 2.0 cm. Diameter: 0.8 to 1.0 cm. Shape: Elliptic. Color: RHS 145A, RHS 144A and RHS 183A. Extrusion of the styles at bud stage: Absent.
*Corolla*.—Quantity of petals/arrangement: 15 to 20, arranged in several whorls. Corolla height: 1.5 cm to 2.0 cm. Petal length: 3.5 cm. Petal width: 1.4 cm to 1.6 cm. Petal shape: Spoon-shaped. Petal apex: Obtuse. Petal base: Acute. Petal margin: Crenate. Depth of petal margin: Medium. Petal texture: Upper and lower surfaces: Smooth. Petal color: Immature: Upper surface: RHS 53A is the base color and RHS 61C is the secondary color along the margin. Lower surface: RHS 63B and RHS 56A. Mature: Upper surface: RHS 59A and RHS 67C. Lower surface: RHS 56B and RHS 70C. Calyx: Quantity of sepals/arrangement: 5, fused. Calyx height: 1.8 cm to 2.0 cm. Calyx diameter, at the apex: 0.8 cm to 1.0 cm. Calyx shape: Campanulate. Epicalyx: Position of outer lobes in relation to calyx: Adpressed. Outer and inner lobes apex shape: Acute. Epicalyx length: 0.8 cm to 1.0 cm. Sepal texture: Upper and lower surfaces: Smooth. Sepal apex shape: Campanulate. Sepal color: Upper surface: RHS N137C. Lower surface: RHS 145B.

Peduncles:
*Length*.—12.0 to 14.0 cm.
*Diameter*.—0.2 cm.
*Strength*.—Moderate.
*Texture*.—Smooth.
*Color*.—RHS 137A.

Reproductive organs:
*Stamens*.—Quantity: 3 to 5. Filament length: 0.5 cm to 0.7 cm. Filament color: RHS 155B. Anther length: 0.1 cm. Anther diameter: 0.05 cm. Anther color: RHS 19B. Pollen amount: Sparse.
*Pistils*.—Quantity: 1. Pistil length: 0.1 cm. Style length: 1.6 cm to 1.8 cm. Style color: RHS 59A. Number of styles per pistil: 1. Stigma shape: Filamentous. Stigma color: RHS 59A. Ovary size: 0.4 cm to 0.6 cm. Ovary shape: Oval. Overall Ovary color: RHS 145A. Ovary texture: Smooth. Fruits/seeds: None observed.

Disease and insect/pest resistance: No special observations were made.

COMPARISON WITH PARENTAL LINE AND KNOWN VARIETY

'KLEDP14206' is a distinct variety of *Dianthus*. 'KLEDP14206' is distinguished from its parent as described in Table 1:

TABLE 1

Comparison with Parental Lines

| Trait | Variety 'KLEDP14206' | Parent |
|---|---|---|
| Flower Color | Dark pink, purple bicolor | Pink, purple eye |

'KLEDP14206' is most similar to the commercial *Dianthus* plant named commercially known as SuperTrouper 'Oscar' (unpatented). Differences between the two varieties are described in Table 2:

TABLE 2

Comparison with Similar Variety

| Trait | Variety 'KLEDP14206' | Commercial line SuperTrouper 'Oscar' |
|---|---|---|
| Flower Color | Dark pink, purple bicolor | Dark pink with a purple eye |

The invention claimed is:

1. A new and distinct variety of *Dianthus* plant named 'KLEDP14206' as illustrated and described herein.

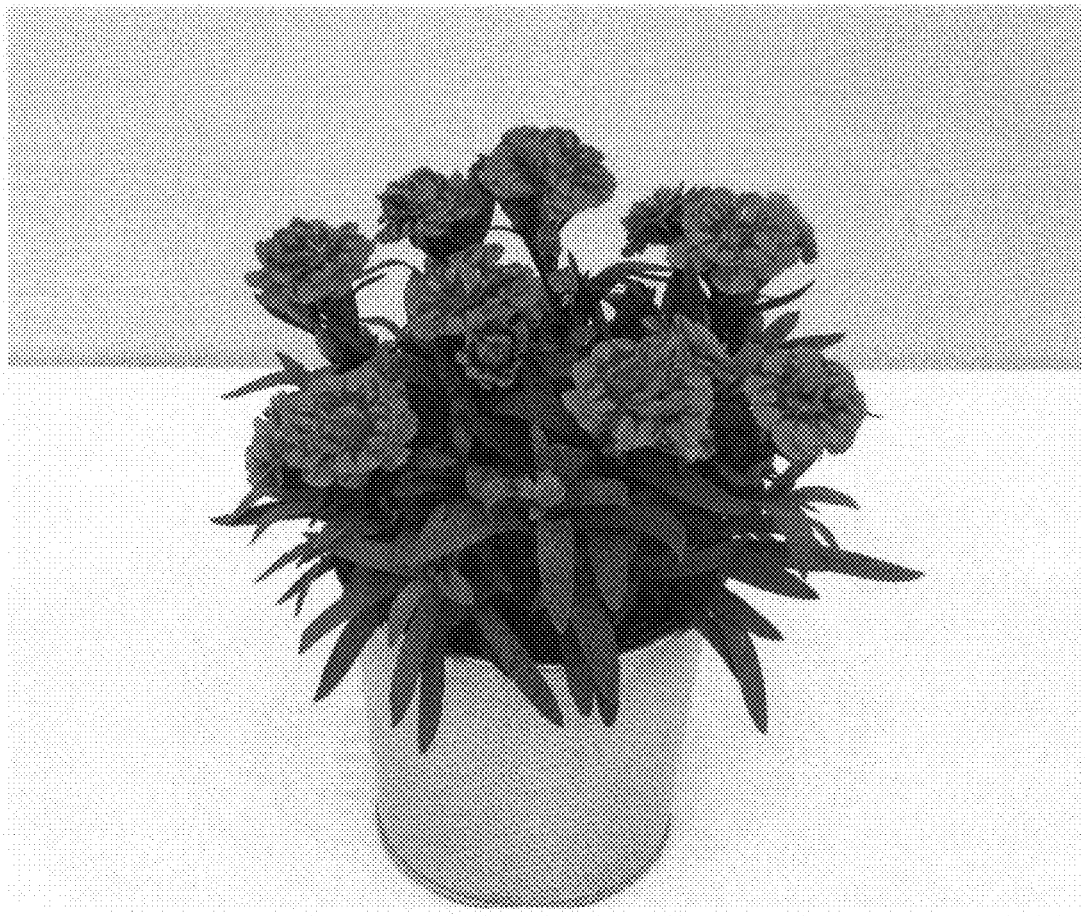

* * * * *